United States Patent
Vernekar et al.

(12) 
(10) Patent No.: US 6,514,748 B1
(45) Date of Patent: Feb. 4, 2003

(54) STRAIN OF STREPTOMYCES FOR THE PREPARATION OF AN ALKALINE PROTEASE INHIBITOR

(75) Inventors: Jui Venkatesh Vernekar, Maharashtra (IN); Mohini Sadanand Ghatge, Maharashtra (IN); Mala Balchandra Rao, Maharashtra (IN); Vasanti Vishnu Deshpande, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/527,602

(22) Filed: Mar. 17, 2000

(30) Foreign Application Priority Data

Mar. 19, 1999 (IN) .......................... 442/DEL/99

(51) Int. Cl.$^7$ ................................. C12N 1/20
(52) U.S. Cl. ................. 435/253.5; 435/71.3; 424/93.43
(58) Field of Search ............................ 435/253.5, 71.3, 435/184; 424/93.43

(56) References Cited

PUBLICATIONS

Uyeda et al., Agric Biol Chem, (1976) 40 (6), 1237–1238.*
Watanabe, et al., Tetrahedron letters, Feb. 1979 No. 7, pp. 625–628.*
Yang et al., Han Guk J Genet Eng, (1987) 2 (1), 13–18.*
Tsuchiya, et al., Agric. Biol. Chem. (1989), 53(3), 841–2.*

\* cited by examiner

*Primary Examiner*—Irene Marx
(74) *Attorney, Agent, or Firm*—Dinesh Agarwal, P.C.

(57) ABSTRACT

The present invention provides a novel strain of Streptomyces sp. having Accession Number PTA 973 and a process for the preparation of an alkaline protease inhibitor employing the said strain.

1 Claim, No Drawings

STRAIN OF STREPTOMYCES FOR THE PREPARATION OF AN ALKALINE PROTEASE INHIBITOR

FIELD

This invention relates to a novel strain of Streptomyces sp. and a process for the preparation of an alkaline-protease inhibitor. More particularly, the invention relates to a process wherein the protease inhibitor exhibiting antifungal properties is produced using a strain of Streptomyces sp. isolated from the soil sample collected from Pune, Maharashtra, India.

BACKGROUND

Protease inhibitors are one of the most abundant classes of proteins in the world. They are found in numerous plants, animals and microorganisms (Kassel et al, Methods in Enzymol. 19, 839, 1970). Protease inhibitors have received increased attention due to the awareness that they control the action of proteases which are of vital importance in regulating many proteolytic processes involved in the mobilization of tissue proteins and in the processing of precursors of proteins. They also serve as an excellent model for studying protein-protein interactions. Based on their ability to inhibit the proteases of insect digestive tracts, protease inhibitors have been implicated to possess defensive role against insects and herbivores (Green and Ryan, Science, 175, 776, 1972). Genes coding for some of the protease inhibitors have been isolated and characterized (Johnson et al., Proc. Natl. Acad. Sci. 86, 9871, 1989, Ryan, Bio Essays, 10, 20, 1989). Direct evidence that the expression of different families of inhibitor genes provides resistance against insect pests has been presented (Hilder et al., Nature, 330, 160, 1987). Protease inhibitors have been the subject of research in many disciplines. Recently, their potential for developing therapeutic agents is being explored. Specific inhibition of the proteases that are crucial in the life cycle of causative microorganisms provides the basis for application of protease inhibitors as therapeutic agents against mortal diseases such as malaria, cancer and AIDS (Billings et al., Proc. Natl. Acad. Sci. 84, 4801, 1987, Seelmeier el al., Proc. Natl. Acad. Sci. 85, 6612, 1988).

Plants and animals are forced to survive and sustain life in a world full of pathogenic bacteria and fungi. Among crop plants, fungal diseases are one of the major biotic stresses that contribute substantially to the overall loss in yield. Fungicides play a vital role in controlling the agricultural economy. Agrochemical industry employs a wide variety of synthetic antifungal agents. However, they are associated with several drawbacks such as (i) the lack of specificity (ii) development of resistance upon prolonged application and (iii) the environmental hazards associated with the residual toxicity. Against this background, biodegradable antifungal agents provide high levels of safety to non-target species. Moreover, they are free from polluting residues and represent a reduced likelihood of developing resistant fungal strains.

Plants exhibit several defense mechanisms against the invading pathogen which can be broadly classified as localized (Staskawicz et. al., Science, 268, 661, 1995) and systemic responses (Boller et al., Planta, 157, 22, 1983). The systemic responses are responsible for accumulation of toxic phytoalexins and pathogenesis related proteins (PRPs). Recently, inhibitors of trypsin and chymotrypsin (Lorito et al., Mol. Plant Microbe Interact. 7, 525, 1994) and of cysteine protease (Joshi et al., Biochem. Biophys. Res. Commun. 246, 382, 1998) of plant origin have been shown to inhibit a few phytopathogenic fungi. Inhibitors of microbial alkaline protease, viz. subtilisin, have been isolated and characterized from microbial sources mainly Streptomyces sp. (Murao & Sato, Agri. Biol. Chem. 36, 160, 1973) and from plant sources (Bodhe, Biochem. Biophys. Acta, 1073, 11, 1990). They have been studied extensively with respect to their structure, mechanism of action and regulation of gene expression. However, none of the above processes provide for preparation of an alkaline protease inhibitor having antifungal properties.

Based on the fact that the alkaline proteases present in the midgut of insect pests play an important role in the digestion of food material, the applicants believe that the inhibitor produced as per the procedure of the present invention using Streptomyces sp. could be a potent inhibitor for proteases particularly alkaline protease, more particularly the proteases of lepidopterean insect pests and therefore, has potential application as a biocontrol agent.

OBJECTS

The main objective of the present invention is to provide a process for the preparation of an alkaline protease inhibitor employing a strain of a newly isolated Streptomyces sp. which was deposited at American Type Culture Collection (ATCC) on Dec. 2, 1999, and bears accession No. PTA 973.

Another object is to provide a biocontrol and anti-fungal agent employing the alkaline protease inhibitor developed according to the process of the invention.

SUMMARY

In accordance with the above and other objects, the invention provides a novel Streptomyces sp. having Accession Number PTA 973. The invention also provides a process for the preparation of an alkaline protease inhibitor, exhibiting anti-fungal properties against a wide spectrum of fungal pathogens and therefore, useful as a biocontrol agent and anti-fungal agent.

DETAILED DESCRIPTION

Accordingly, the invention provides a novel strain of Streptomyces sp. isolated by the Applicants from the soil sample collected from Pune, Maharashtra, India. The strain has been deposited at the American Type Culture Collection, USA, and bears Accession Number PTA 973.

Further, the present invention provides a process for the preparation of an alkaline protease inhibitor, said process comprising the steps of:

(i) growing Streptomyces sp. deposited at American Type Culture Collection, and bearing Accession Number PTA 973, in a fermentation medium comprising assimilable carbon and nitrogen sources at a temperature in the range of 28–30° C. for a period of at least 96 hrs., (ii) separating the solids by conventional methods to obtain cell free liquid, and (iii) recovering the protease inhibitor by conventional precipitation method from the cell free liquid using salting out agent.

In an embodiment, the fermentation medium comprises carbon and nitrogen sources and micro-ingredients.

In another embodiment, the carbon source is selected from starch glycerol, glucose, sucrose, mannose, lactose and sorbitol.

In yet another embodiment, the nitrogen source is selected from casein, asparagine potassium nitrate, skimmed milk, soyabean meal, yeast extract, malt extract, peptone, casamino acids and urea.

In a further embodiment, the medium may be supplemented with salts of metals such as Na, K, Ca, Mg, Fe, etc. in the form of their sulfates, phosphates or carbonates.

In a feature, the fermentation medium further comprises

| 1) Starch | 0.5–1% |
|---|---|
| 2) Casein | 0.05–0.1% |
| 3) potassium nitrate | 0.1–0.2% |
| 4) sodium chloride | 0.1–0.2% |
| 5) dipotassium hydrogen phosphate | 0.1–0.2% |
| 6) magnesium sulfate | 0.002–0.005% |
| 7) calcium carbonate | 0.001–0.002% |
| 8) ferrous sulfate | 0.001% |

In another embodiment, the salting out agent is ammonium sulfate.

Production of the inhibitor and its activity is also dependent upon the nature and composition of media components, inoculum size and parameters such as aeration, agitation, etc. Optimum growth and production of the protease inhibitor is obtained after 96–120 h of growth when a 5–15% (v/v) log phase inoculum is employed. Post fermentation processing of the broth for the isolation of the protease inhibitor includes centrifugation or filtration. The cell free supernatant is treated with ammonium sulfate to precipitate the proteinaceous inhibitor. The salted out inhibitor is recovered by centrifugation. The resulting product is subjected to preparative polyacrylamide gel electrophoresis (PAGE).

In another feature, the protease inhibitor produced in the fermentor medium is separated by conventional methods like filtration or centrifugation.

In yet another feature, the protease inhibitor in the cell-free culture filtrate is purified by employing various methods. The inhibitor protein is precipitated by salting out by the addition of ammonium sulfate. The precipitated protein is dissolved in buffer, dialyzed and concentrated by vacuum evaporation. The concentrated inhibitor is loaded on the preparative polyacrylarnide gel electrophoresis (PAGE) and the inhibitor band is detected by gel X-ray film contact print method (Pichare and Kachole, J. Biochem. Biophys. Methods, 28, 215, 1994). The protein corresponding to the protease inhibitor is extracted from gel, dialyzed and concentrated. The homogeneity of the protein is determined by native and SDS-PAGE and by gel filtration on HPLC. One unit of inhibitor is defined as the amount of inhibitor which inhibits the protease activity expressed in terms of decrease in optical density at 280 nm of 0.001 per minute.

Without wishing to be bound by any theory, the Applicants state that the protease inhibitor developed in accordance with the process of the invention has exhibited anti-fungal properties against a wide spectrum of fungal pathogens such as fusarium, Alternaria, Trichoderma sp and Rhizoctina. Therefore, the protease inhibitor has potential use as an effective biocontrol and anti-fungal agent.

Characteristics of the Novel Streptomyces Strain

The Streptomyces sp. used in this invention for production of alkaline protease inhibitor (API) has been newly isolated from soil sample collected in Pune city, India. The enrichment medium designed for actinomycetes was used for the isolation. Pure culture was obtained by single colony plating technique. Typical colonies with firm, leathery substrate mycelium were formed in the early stages of the development followed by the formation of loose, cottony aerial mycelium bearing spores of gray color. The colonies possess strong odor of damp earth on the laboratory media.

The scanning electron micrographs of the organism revealed that it has a branching mycelium with conidia produced in chains on top of the aerial hyphae. Mature spore chains, with approximately 10 to 50 spores per chain, were found arranged in spirals. Spores bear a spiny surface. These observations are characteristic of the organism belonging to the order Actinomycetales, genus Streptomyces.

The alkaline protease inhibitor described in this invention is produced by a newly isolated Streptomyces sp. An alkaline protease inhibitor having novel antifungal properties specifically towards phytopathogenic fungi has not been reported earlier. The Streptomyces sp. employed in the invention is deposited at American Type Culture Collection, USA and bears accession No.PTA-973. The organism is found to be an aerobic actinomycete having a branching mycelium with conidia produced in chains from the aerial hyphae, mature spore chains, generally 10 to 50 spores per chain are arranged in spirals. Spores are of pale gray colour with spiny surface.

The process for the preparation of the alkaline protease inhibitor is carried out by conventional methods for the preparative polyacrylamide gel electrophoresis followed by gel X-ray film contact print technique for the detection of an inhibitor band which was used intentionally for single step purification.

Optimization of medium conditions for maximum production of the alkaline protease inhibitor was carried out by replacement of the casein and starch medium with different carbon and nitrogen sources. The various carbon sources (1%) used were glucose, sucrose, mannose, lactose and sorbitol. The nitrogen sources (0.1%) tested were skimmed milk, soyabean meal, yeast extract, malt extract, beef extract, peptone, casamino acids and urea. Maximum production of the alkaline protease inhibitor was obtained in the medium containing starch and casein as carbon and nitrogen source respectively.

The process of the present invention is described herein below with reference to examples, which are illustrative only and should not be construed to limit the scope of the present invention in any manner.

EXAMPLE 1

Seven days old agar slant culture of Streptomyces sp. was inoculated into medium containing 1% starch, 0.1% casein, 0.2% potassium nitrate and supplemented with salts of metals of Na, Ca, Mg, Fe in the form of their sulfates, phosphates, carbonates etc. at a pH of 7.0–7.5 and incubated for 48 h at 28° C. on a rotary shaker (200 rpm.) 10% (v/v) vegetative inoculum was transferred to a similar medium. After 96 h maximum protease inhibitory activity of 0.406 U/ml was obtained.

EXAMPLE 2

The cell free culture filtrate recovered by centrifugation was fractionally precipitated with ammonium sulfate. The precipitated protein was dissolved in buffer and dialyzed against 10 mM phosphate buffer pH 7.5 and concentrated by lyophilization. The concentrated crude protein was loaded on preparative polyacrylamide gel electrophoresis. The protease inhibitor band was detected by gel X-ray film contact print method. The protein corresponding to protease inhibitor was extracted from the gel, dialyzed and concentrated. It was homogeneous on native and SDS-PAGE and eluted as a single peak by gel filtration on HPLC.

EXAMPLE 3

The protease inhibitory activity of the crude as well as the purified alkaline protease inhibitor was detected by a plate assay. The assay was carried out in petri-plates containing milk agar with well made in the center and at a distance of 1 cm from the center. 20 μl of the enzyme solution (subtilisin, 1 mg/ml) was added in the central well. An appropriate concentration of the purified protease inhibitor was added in one well and sterile distilled water as a control in the other well. The plates were incubated at 37° C. The inhibition of hydrolysis of casein by the protease shown by the absence of clearance zones around the purified inhibitor protein indicated protease inhibitory activity.

EXAMPLE 4

This example exhibits the antifungal activity of the protease inhibitor. The fungal strains *Trichoderma reesei* (NCIM 992, 1051, 1052, 1186), *Fusarium oxyspqrum* (NCIM 1008, 1043, 1072), *Fusarium moniliforme* (NCIM 1100, 1099) and *Alternaria alternata* (NCIM 887) obtained from the in-house culture collection unit, National Collection of Industrial Microorganisms (NCIM), Pune, India were grown on agar slants for 7–8 days. Fungal mycelium from freshly grown culture was inoculated at the centre of petri plates containing Sabouraud's dextrose-agar medium and incubated at 28–30° C. for about 48 h to allow mycelial vegetative growth. On the periphery of the advancing fungal mycelia, sterile filter paper discs impregnated with different concentrations of crude and purified protease inhibitor were placed. The plates were further incubated at room temperature and observed for crescents of retarded mycelial growth.

The crude culture filtrate as well as the purified protease inhibitor strongly inhibit the mycelial spread of *Trichoderma*, sp., *Fusarium oxysporum* and *Fusarium moniliforme*. The fungal strains tested for determination of the antifungal activity in example 4 hace the characteristics corresponding to strains deposited at international depositories with the following accession numbers.

| Fungal Strain | NCIM No. | International Depository No. |
|---|---|---|
| *Fusarium oxysporum* | 1008 | CMI 107510b |
| | 1043 | CMI 113138 |
| | 1072 | IFO 5009 |
| *Fusarium moniliforme* | 1099 | ATCC 12616; CMI 58290 |
| | 1100 | ATCC 14164; CMI 112801 |
| *Alternaria alternata* | 887 | ATCC 11785 |
| *Trichoderma reesei* | 1186 | ATCC 26921 |
| | 1052 | ATCC 24449 |
| | 992 | ATCC 13631; CMI 45548 |
| *Fusarium oxysporum* f.sp. *ciceri* | 1281 | Race1, Deposited by Dr. M. P. Haware ICRISAT, India. Causes wilt of chickpea (*Cicer arientum L*) (ref: Plant Disease 66, 809, 1982) |

ATCC: American Type Culture Collection, USA
CMI: Commonwealth Mycological Institute, New Surrey, U.K.
IFO: Institute of Fermentation, Osaka, Japan.
NCIM: National Collection of Industrial Microorganisms, Pune, India
ICRISAT: International Crop Research Institute for Semi Arid Tropics, Andhra Pradesh, India.

EXAMPLE 5

Antifungal activity of API was assessed by inhibition of the growth of fungi as determined by a hyphal extensive inhibition assay. The crude inhibitor preparation was checked for its ability to inhibit fungi mycelial extension. The fungi namely *Fusarium oxysporum, Fusarium moniliforme, Alternaria alternata, Trichoderma reesei* exhibited moderate to good inhibition by the crude preparation of the inhibitor. *Fusarium oxysporum* f. sp. *ciceri* was the most sensitive to inhibition requinng 30 μg/disc (1 mg/ml) as minimum inhibitory does (MID). *Trichoderma reesei* (NCIM 1186) required a MID of 100 μg/disc (4mg/ml) while other strains required much higher doses of about 10 mg/ml. Purified API showed a 100 fold increase in antifungal activity over the crude inhibitor preparation against *Fusarium oxysporum* requiring a MID of 0.5 μg/disc.

The phytopathogenic fungal strain *F. oxysporum* f. sp. *ciceri* when grown in liquid medium produces extra cellular alkaline protease. Inhibition of the alkaline protease was observed in the presence of API (0.42 U/ml of inhibition) as determined by Kunitz caseinolytic assay. This observation suggests that the antifungal activity of API is a result of the inhibition of the protease which is indispensible for the growth and development of the organism.

ADVANTAGES

1. The microbial protease inhibitor reported in the present invention shows the inhibition of the alkaline proteases such as subtilisin, proteinase K and other fungal alkaline proteases. Alkaline proteases are present in the midgut of the insect pests and play a crucial role in the digestion of the food material. As the inhibitor has the potential to inactivate alkaline proteases, it has a potential application as a biocontrol agent.
2. The protease inhibitor strongly inhibits the mycelial spread of some phytopathogenic fungi and therefore can be an effective antifungal agent.
3. The protease inhibitor, being proteinaceous in nature, is biodegradable and hence is environment-friendly as compared to chemical pesticides which have residual toxicity.
4. The protease inhibitor being of microbial origin, offers an attractive and economical process for its rapid and convenient production. Moreover, it would be easier to manipulate the microbial protease inhibitor than those from plants or animals sources.
5. The novelty of the process resides in the production from a newly isolated *Streptomyces sp.* of an alkaline protease inhibitor exhibiting antifungal properties, specifically against agronomically important fungal pathogens such as Fusarium, Alternaria and Rhizoctonia. The merit of this product (alkaline protease inhibitor) is that it is a biodegradable and environmentally friendly antifungal agent as against toxic chemical fungicides used currently. The alkaline protease inhibitor described in this process is stable over a wide range of pH (6 to 12) and temperature (40 to 95° C.). Therefore one can envision the direct application of the inhibitor as a biocontrol agent for the protection of plants against phytopathogenic fungi by encapsulation for surface application or can be sprayed directly. Furthermore the alkaline protease inhibitor being of microbial origin, offers an attractive and economical process for its rapid and convenient production. Moreover, transfer of the protease inhibitor gene to the desired plants will result in the generation of transgenic plants that are tolerant/resistant to the attack of phytopathogenic fungi.

What is claimed is:

1. A biologically pure culture of a Streptomyces sp. strain having accession number PTA 973 and deposited at American Type Culture Collection, USA.

* * * * *